(12) United States Patent
Bove

(10) Patent No.: US 9,114,439 B2
(45) Date of Patent: Aug. 25, 2015

(54) SHOE SANITATION DEVICE

(71) Applicant: John David Bove, Suwanee, GA (US)

(72) Inventor: John David Bove, Suwanee, GA (US)

(*) Notice: Subject to any disclaimer, the term of this patent is extended or adjusted under 35 U.S.C. 154(b) by 0 days.

(21) Appl. No.: 13/840,281

(22) Filed: Mar. 15, 2013

(65) Prior Publication Data

US 2014/0259482 A1    Sep. 18, 2014

(51) Int. Cl.
*A47L 23/22*    (2006.01)
*B08B 1/00*    (2006.01)

(52) U.S. Cl.
CPC ............... *B08B 1/006* (2013.01); *A47L 23/22* (2013.01); *A61L 2202/15* (2013.01)

(58) Field of Classification Search
CPC ...................................................... A47L 23/22
USPC ............................................. 15/215, 216, 238
See application file for complete search history.

(56) References Cited

U.S. PATENT DOCUMENTS

| | | |
|---|---|---|
| 3,300,275 A | 1/1967 | Lorman |
| 4,793,018 A | 12/1988 | Ehrich |
| 5,164,164 A | 11/1992 | Strickler et al. |
| 5,597,418 A * | 1/1997 | Evans et al. ........................ 134/6 |
| 5,771,528 A * | 6/1998 | Nappi, Sr. ........................ 15/311 |
| 5,881,427 A * | 3/1999 | Offner ............................. 15/215 |
| 6,463,885 B1 | 10/2002 | Laner |
| 6,651,288 B1 * | 11/2003 | Hackett ....................... 15/104.92 |
| 7,741,263 B2 | 6/2010 | Kilkenny et al. |
| 8,533,888 B2 * | 9/2013 | Kessler ....................... 15/104.92 |
| 2004/0078909 A1 * | 4/2004 | Coppa ......................... 15/104.92 |
| 2006/0009369 A1 | 1/2006 | Kilkenny et al. |
| 2006/0107479 A1 * | 5/2006 | Forrest ......................... 15/210.1 |
| 2006/0151516 A1 * | 7/2006 | Etheridge et al. ............... 221/45 |
| 2009/0098031 A1 | 4/2009 | Crist |
| 2010/0296970 A1 | 11/2010 | Trimarco et al. |
| 2013/0075416 A1 * | 3/2013 | Boyce .............................. 221/34 |

FOREIGN PATENT DOCUMENTS

| | | | |
|---|---|---|---|
| JP | 6-90891 | * | 4/1994 |
| JP | 6-169876 | * | 6/1994 |

* cited by examiner

*Primary Examiner* — Randall Chin
(74) *Attorney, Agent, or Firm* — Russel L. Sandidge

(57) ABSTRACT

A device for disinfecting the soles of shoes or feet is disclosed. The device contains a spool of sanitizing wipe stretched across an opening. The user may step into the opening to sanitize shoe or foot soles, and also may wind the sanitizing wipe spool to reveal a fresh, unused portion of sanitizing wipe. The device may also contain a second opening that allows access to a drying material.

17 Claims, 3 Drawing Sheets

SHOE SANITATION DEVICE

TECHNICAL FIELD

The present invention relates generally to sanitizing, and, more specifically, the present invention relates to a device providing a renewable, sanitized surface for sanitizing the soles of footwear and/or feet and optionally provides a means for drying any sanitizing fluid from said shoes or feet.

BACKGROUND OF THE INVENTION

Advances in medical research have revealed that one may constantly come into contact with various germs, such as bacteria, viruses and other types of harmful microorganisms through their everyday activities. In addition, these various germs may then be spread to other people that one has contact with, or simply people who contact various surfaces that other people have previously infected with germs.

While most bacteria are harmless, many disease-causing bacteria produce toxins that damage cells and cause illness. Viruses invade cells in the body, affecting the workings of the cell. Neither these, nor other microorganisms, are generally desirable to most people on their skin or their surrounding environment. Further, unlike most healthy people that generally harbor some microorganisms within their system, individuals having auto-immune deficiencies cannot tolerate this and are especially susceptible to even trace amounts of microorganisms.

In an effort to combat these germs and avoid spreading them, many people use sanitizing, antibacterial gels or wipes to clean their hands and other body parts that may have come into contact with germs, and also to clean surfaces that may contain germs. However, one area that tends to get overlooked in the battle against germs is the bottom of our feet, or, more specifically, the soles of our shoes.

Floors, sidewalks, open ground, and the like, are breeding grounds for a large variety of germs. People are constantly dropping or spilling items onto the floor, and as people walk through any type of germ-infected area, the germs are rapidly spread by the soles of everyone's feet. While many people manage to avoid contact with surfaces intended for your hands—such as handrails or doors—no one who is able to walk can avoid contacting the ground with their shoes. Thus, the bottoms of our shoes and/or feet can become infected with an enormous variety of germs contacted throughout the day. Then, when one comes home after a day of walking around the office, a hospital, a subway, or any public area, all of those potential germs are brought back to the home.

Regular door mats do little to solve the problem of germs coming into the household on the soles of shoes. These door mats generally include a rough material on their surface to brush the dirt off. However, many of the bacteria or other microorganisms remain alive on the soles and are brought into the household.

Numerous approaches have been taken to the use of cleaning devices for shoes at the entry to homes, businesses or specific areas of a building that are required to remain free of germs and debris. For example, U.S. Pat. No. 3,300,275, issued to Lorman, proposes a floor tray with a grate, which can be depressed and cause a washing solution to saturate the sole and lower part of the shoe. U.S. Pat. No. 5,164,164, issued to Strickler et al. and U.S. Published Patent Application 2009/0098031 similarly propose reservoirs of cleaning solution that are activated by stepping onto a tray. Another approach, found in U.S. Pat. No. 5,881,427, issued to Offner, is a floor mat or grate placed over a tray having disinfectant, wherein the grate is overlain with a fabric that may absorb the disinfectant and allow the user to clean his shoes by stepping on the dampened fabric. Another potential solution utilizes a foot tray with an upstanding wick saturated with a cleaning solution along with an absorbent mat for the wearer to use in drying off each shoe. Still another approach utilizes a separate scraper along with a separate cleansing solution to be used in successive steps in cleaning each shoe.

Most of these proposed methods are insufficient, in part because the cleaning device becomes infected with the germs of each user, and there is either no means to remove the germs, or the means for removing the germs is not convenient enough to be operated after every user. Thus, some of the germs from each user remain behind, and could actually infect the shoes of the next user, rather than removing the second user's germs. Another drawback with these prior devices is that the germicide solution remains on the soles of the shoes, and could cause a safety issue with potential slipping.

Thus, there is a need for a device for sanitizing soles of shoes and/or feet that provides a renewable surface to prevent contact with the germs of prior users, and also may provide a sanitized means for drying the soles of the clean shoes to eliminate potential slipping.

SUMMARY OF THE INVENTION

Briefly described, in a preferred embodiment, the present invention overcomes the above-mentioned disadvantages and meets the recognized need for such a device by providing a sanitizing device having at least one opening where a user may stand to sanitize the user's shoe soles. The opening contains a form of sanitizing antibacterial wipe upon which the user rubs their feet to clean the soles of their shoes. The sanitizing wipe may be replaced after every user, so each user is confronted with a fresh, uncontaminated wipe.

In another embodiment of the invention, the sanitizing wipe is in the form of a spool that may be rolled to reveal fresh, unused portions of the wipe. The user may renew the section of wipe accessible from the opening by turning the spool to move a used portion of the wipe past the opening and reveal a new section of wipe.

In a preferred embodiment of the present invention, the spool may be turned by a ratchet mechanism. In yet another embodiment, the ratchet system is activated by a ratchet knob, and, in another embodiment, the knob may be turned by pulling a handle convenient to the user.

In yet another embodiment of the invention, the sanitizing wipe is provided in the form of a replaceable canister, so that once the wipe is used up the canister may be discarded and replaced with a new canister.

In still another embodiment, the device further provides a drying section that utilizes a drying material instead of a sanitizing wipe. In a preferred embodiment, the drying material is renewable and replaceable in the same manner as the sanitizing wipe.

For another optional embodiment, the device further provides one or more covers for the cleaning and/or drying sections, which covers those sections when the device is not in use. The cover may provide protection for the sanitizing wipe or drying material, to assist in avoiding contamination, and preferably prevent or delay the unused wipes from drying out. In a preferred embodiment, the covers may be connected to the ratchet device, so that the cover opens up to reveal the fresh surface area for cleaning simultaneously with advancing the cleaning or drying material.

These and other objects, features, and advantages of the invention will become more apparent to those ordinarily skilled in the art after reading the following Detailed Description and Claims in light of the accompanying drawing Figures.

BRIEF DESCRIPTION OF THE DRAWINGS

Accordingly, the present invention will be understood best through consideration of, and reference to, the included Figures, viewed in conjunction with the Detailed Description of the Invention referring thereto, in which like reference numbers throughout the various Figures designate like structure and in which.

It is to be noted that the drawings presented are intended solely for the purpose of illustration and that they are, therefore, neither desired nor intended to limit the invention to any or all of the exact details of construction shown, except insofar as they may be deemed essential to the claimed invention.

DETAILED DESCRIPTION OF THE INVENTION

In describing preferred embodiments of the present invention illustrated in the Figures, specific terminology is employed for the sake of clarity. The invention, however, is not intended to be limited to the specific terminology so selected, and it is to be understood that each specific element includes all technical equivalents that operate in a similar manner to accomplish a similar purpose.

In accordance with the present invention, a housing device is provided that may house a spool of sanitary antibacterial wipes sufficient for cleaning germs and bacteria from the soles of shoes and/or feet. The housing device provides access to the sanitary wipes so that soles may easily be cleaned, and a means for renewing the sanitary wipes, so that used wipes are moved out of the way and fresh sanitary wipes are provided for the next user.

Figure 1:
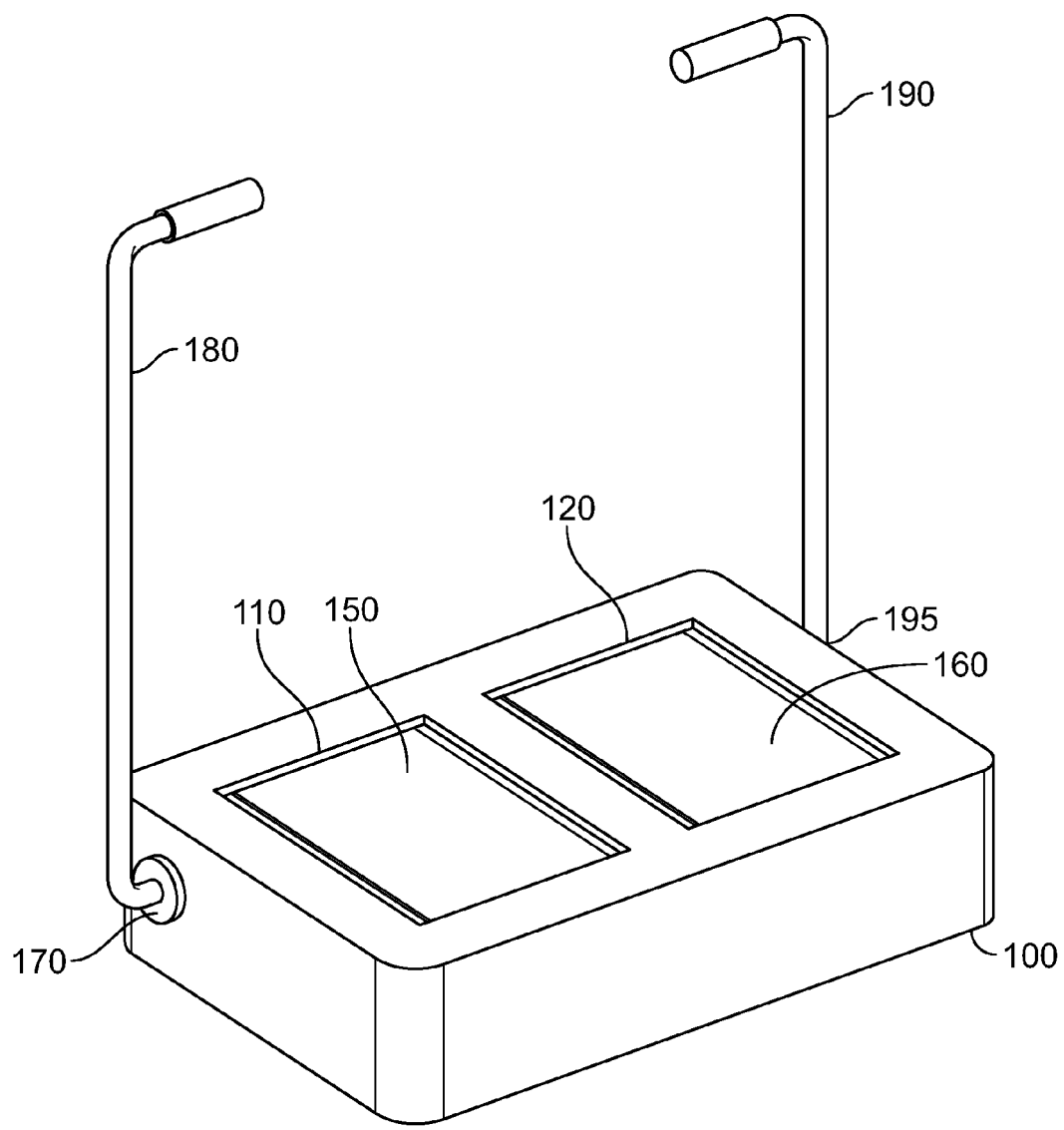
FIG. 1 is a perspective view of a device that embodies many features of the present invention.

Turning now to FIG. 1, one such device 100 contemplated by the present invention is shown. Device 100 contains at least one opening 110, where a user may stand to sanitize the soles of the user's shoes. Device 100 may optionally contain at least one second opening 120 for drying the user's soles, as will be discussed in more detail below. Focusing now on the sanitizing opening 110 of device 100, opening 110 provides access to renewable sanitizing wipe 150. The composition of sanitizing wipe 150 will be disclosed more fully below. The user may step into opening 110 and move his or her feet to effectively sanitize their soles.

One convenient aspect of the present invention is the ability to easily renew or replace the used portion of sanitary wipe 150 after the user has cleaned their soles. It is contemplated that sanitary wipe 150 may be in the nature of a large spool of sanitary wipe material, so that after use the spool may be rolled to expose a new, unused portion of sanitary wipe 150 for the next user. One possible means for rolling the spool is shown in FIG. 1, which illustrates ratchet knob 170 connected to handle 180. With this configuration, a user may pull handle 180, thereby moving ratchet knob 170, causing the spool of sanitary wipe 150 to roll sufficiently to expose a new section of wipe within sanitary opening 110.

Depending upon the type of solution used with sanitary wipe 150, the soles of the user's shoes may be slightly damp or slippery after utilizing the sanitation device. Thus the present invention also provides for an optional drying opening 120 as part of device 100. Drying opening 120 provides an opportunity for the users to dry the soles of their shoes before stepping onto the floor. One possible means for drying the soles would be to provide a drying material 160, possibly in the same type of spool arrangement as may be used with sanitary wipe 150. In such a configuration, drying material 160 might also be advanced along its spool utilizing a ratchet knob 195 connected to handle 190.

Figure 4:
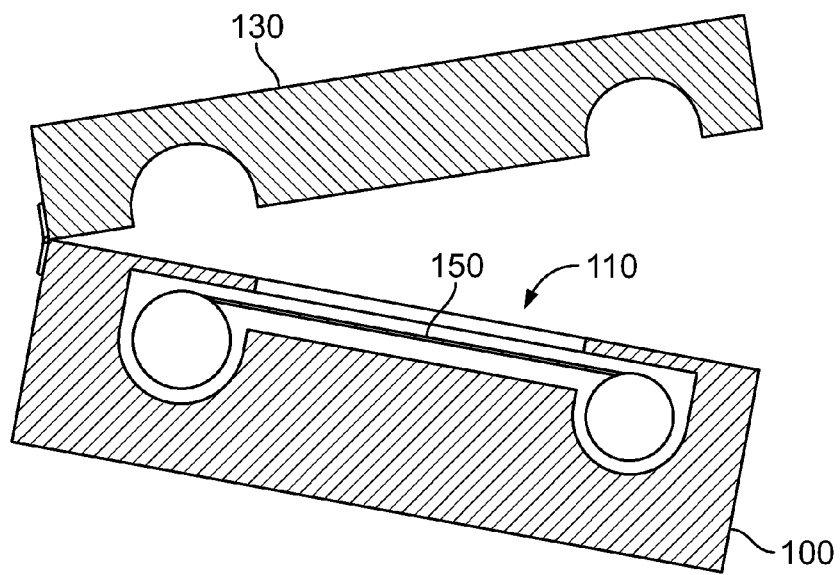
FIG. 4 is a cutaway side view of one embodiment showing a lid attached to the main body of the device.
Figure 5:
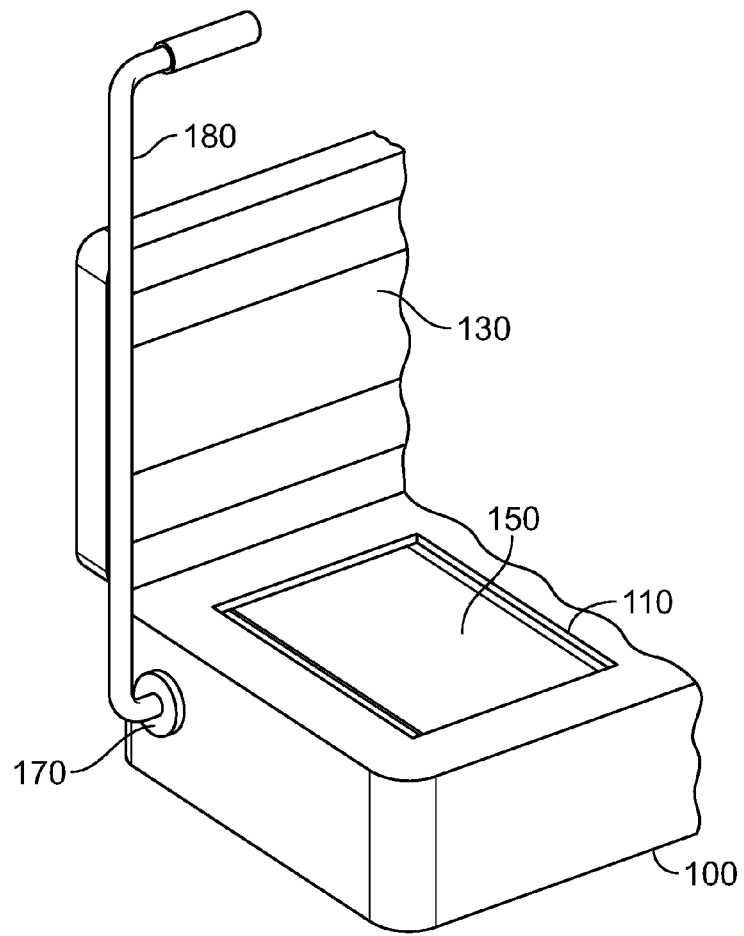
FIG. 5 is a perspective view of a partial device showing the optional lid.

In an alternative embodiment of the present invention illustrated in FIGS. 4 and 5, the device may also utilize cover 130 to cover sanitary opening 110 and optional drying opening 120 when the device is not in use. An additional option would provide separate covers for each opening 110 and 120. (The separate cover option is not illustrated). Cover 130 may assist in keeping the sanitary wipe 150 and drying material 160 clean from debris. Cover 130 would be opened whenever the user is preparing to use the device. Cover 130 may optionally be connected to handles 180 and/or 190 so that moving the handles causes the cover to open, and also causes the cleaning surfaces to be ratcheted to a new position.

Figure 2:
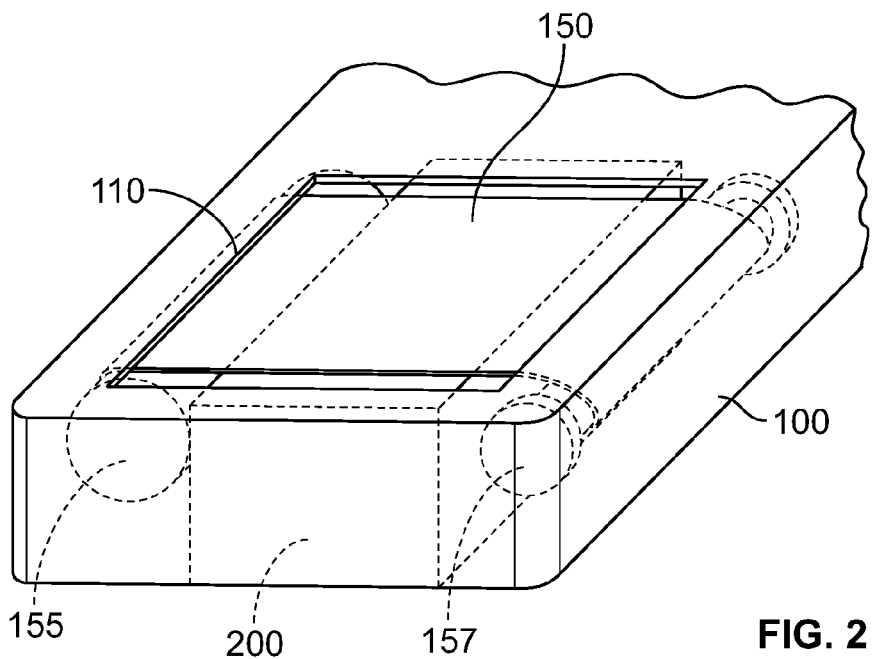
FIG. 2 is an alternative view of the device in FIG. 1, illustrating some of the internal mechanizations that may be utilized for the present invention.

Turning now to FIG. 2, an illustration of the internal mechanism of device 100 is shown to better illustrate one type of spooling mechanism that may be used in conjunction with openings 110 and 120. Inside opening 110 is canister 155 which contains a full roll of sanitizing wipe 150. Sanitizing wipe 150 may be pulled out of canister 155 and attached to spool 157. In this way, a section of wipe 150 will be exposed to opening 110 where it may be accessed by a user. Once the section of wipe 150 has been used, the wipe may be rolled onto spool 157 to pull a fresh section of wipe 150 into opening 110. Such renewal of sanitizing wipe 150 may continue after each use, until the entire roll of wipe 150 has been used. Also shown in this figure is platform 200 that is underneath sanitizing wipe 150. Platform 200 provides a place for the user to stand and create pressure between the soles of the user's shoes and sanitizing wipe 150 and allow for cleaning. Platform 200 may be constructed of any type of shape and material, and may conceivably be designed in a way to assist in maximizing contact between a sole and sanitizing wipe 150, such as, by forming the platform in the general shape of a shoe sole.

Figure 3:
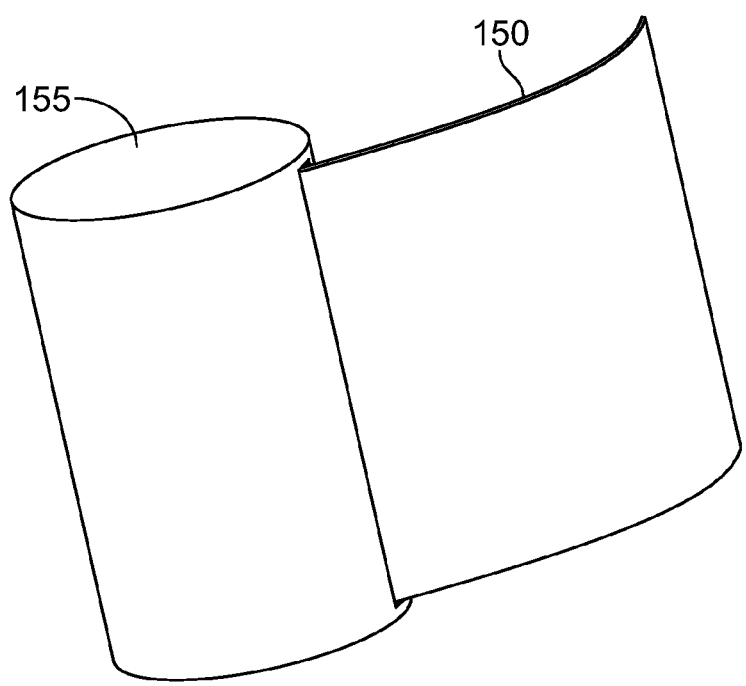
FIG. 3 illustrates a container of sanitary wipes that may be used in connection with the present invention.

One convenient aspect of the present invention is the ability to design the device so that a used spool of wipe 150 may be easily replaced. FIG. 3 illustrates a canister 155 and spool of sanitizing wipe 150 that may be used with the present invention. As shown, canister 155 may contain a large spool of sanitizing wipe 150, with an opening on the side so that a length of wipe 150 may be pulled from the side of canister 155. Such canisters may be sold separately from device 100, providing a convenient means to continually replace the used spool of sanitizing wipe 150. Referring back to FIG. 2, canister 155 may be placed at one end of opening 110, then a length of sanitizing wipe 150 pulled across platform 200, followed by attaching the end of wipe 150 to spool 157. Alternatively, spool 157 may also be a disposable item packaged with canister 155, so that a user just places canister 155 and spool 157 into device 100, and sanitizing wipe 150 is thereby automatically in place.

Any known means may be utilized to roll spool 157 and expose a new surface of sanitizing wipe 150 to opening 110. FIG. 1 illustrates just one means contemplated by the present invention. This means utilizes a ratchet system that is activated by ratchet knob 170. The knob may be turned by pulling on handle 180. After the user cleans the soles of his/her shoe, handle 180 may be pulled to activate the ratchet system and cause spool 157 to pull the used section of sanitizing wipe 150 across the opening and onto the spool, thereby exposing a fresh section of wipe 150. The present invention is intended to encompass any means for rotating the spool to expose new portions of the wipe material, such as a knob allowing for turning the spool by hand, a ratchet system connected to such a knob, or an electronic means operated by, for example, a push button or motion detector.

Sanitary wipes are already well-known, and the invention is not intended to be limited by the use of any particular type of wipes. The only requirements for the present invention are that the carrier fabric of the wipe be sufficiently strong to withstand the wiping motion of a user's feet, and that the sanitizing formula be strong enough to substantially reduce the amount of germs and other microorganism that would reasonably be expected to appear on one's shoe soles. Examples of sanitizing solutions that may be useful for the present invention are disclosed in U.S. Pat. No. 7,741,263 B2 issued to Kilkenney on Jun. 22, 2010, the contents of which are hereby incorporated by reference.

Depending upon the composition of sanitary wipe 150, a user may desire to dry the soles of his/her feet before stepping onto the floor. Therefore, device 100 may also include drying opening 120. It is contemplated that drying opening 120 may operate substantially the same as sanitizing opening 110, except that a drying material 160 would be used in place of sanitizing wipe 155. If desired, the drying section could similarly use a canister and spool system to expose fresh, clean portions of drying material 160 to opening 120. The system may be designed to include a similar optional ratchet system, operated by ratchet knob 195 and handle 190.

Having thus described exemplary embodiments of the present invention, it should be noted by those skilled in the art that the disclosures herein are exemplary only and various other alternatives, adaptations, and modifications may be made within the scope and spirit of the present invention. Accordingly, the present invention is not limited to the specific embodiments as illustrated herein, but is only limited by the following claims.

What is claimed is at least:

1. A device for sanitizing a user's soles comprising:
at least one opening in which a user may place a foot, said opening containing a sanitizing material that comprises a formulation for substantially sanitizing the soles of shoes;
a providing spool and a disposing spool, wherein the sanitizing material is connected to the providing spool and the disposing spool, such that the sanitizing material may be wound off of the providing spool and onto the disposing spool to position a fresh portion of the sanitizing material to the at least one opening; and
means for a user to rotate the disposing spool to wind used sanitizing material onto the disposing spool;
wherein, the providing spool is housed within a canister that may be removed from the device, the canister having a lengthwise opening through which the sanitizing material may be wound off of the providing spool.

2. The device of claim 1, wherein the disposing spool is rotated by use of a ratchet system.

3. The device of claim 2, wherein the ratchet system is activated by moving a handle.

4. The device of claim 3 further comprising a cover hingeably attached to the device such that the cover may be opened to provide access to the opening and closed when the device is not in use and wherein the cover is actively connected to the handle so that the cover will open and close upon use of the handle.

5. The device of claim 1, wherein the disposing spool is rotated by electronic means.

6. The device of claim 1, further comprising a second opening, said second opening containing a drying material for drying the soles of the user.

7. The device of claim 6, wherein the drying material is connected to a second providing spool and a second disposing spool, such that the drying material may be wound off of the second providing spool and onto the second disposing spool to position a fresh portion of the drying material to the second opening.

8. The device of claim 7, wherein the second disposing spool may be rotated by a user to pull a portion of used drying material onto the second disposing spool.

9. The device of claim 8, wherein the second disposing spool is rotated by use of a ratchet system.

10. The device of claim 9, wherein the ratchet system is activated by moving a handle.

11. The device of claim 8, wherein the second disposing spool is rotated by electronic means.

12. The device of claim 1 further comprising a cover hingeably attached to the device such that the cover may be opened to provide access to the opening and closed when the device is not in use.

13. The device of claim 12 in which the cover is designed so that when the cover is in the closed position the evaporation rate of the sanitizing formulation is substantially reduced.

14. The device of claim 1 further comprising a support platform underneath the sanitizing material.

15. The device of claim 14 wherein the top of the support platform is shaped substantially like the sole of a shoe.

16. The device of claim 1 wherein the canister is disposable.

17. The device of claim 1 wherein the device is designed so that the providing spool canister may be removed and replaced with a new providing spool canister.

\* \* \* \* \*